(12) United States Patent
Bar-Cohen et al.

(10) Patent No.: US 6,406,429 B1
(45) Date of Patent: Jun. 18, 2002

(54) DETECTION OF CYSTIC STRUCTURES USING PULSED ULTRASONICALLY INDUCED RESONANT CAVITATION

(75) Inventors: Yoseph Bar-Cohen, Seal beach, CA (US); John S. Kovach, New York, NY (US)

(73) Assignees: City of Hope, Duarte; California Institute of Technology, Pasadena, both of CA (US)

( * ) Notice: Subject to any disclaimer, the term of this patent is extended or adjusted under 35 U.S.C. 154(b) by 0 days.

(21) Appl. No.: 09/644,096

(22) Filed: Aug. 23, 2000

Related U.S. Application Data

(60) Provisional application No. 60/149,901, filed on Aug. 23, 1999.

(51) Int. Cl.[7] .................................................. A61B 8/00

(52) U.S. Cl. ...................................................... 600/438

(58) Field of Search ................................ 600/438–439, 600/443, 437; 601/2–11

(56) References Cited

U.S. PATENT DOCUMENTS

| | | | | |
|---|---|---|---|---|
| 5,018,508 A | * | 5/1991 | Fry et al. ........................ | 601/3 |
| 5,209,221 A | * | 5/1993 | Riedlinger ...................... | 601/3 |
| 5,219,401 A | * | 6/1993 | Cathignol et al. .............. | 601/3 |
| 5,368,032 A | * | 11/1994 | Cline et al. ..................... | 601/3 |
| 5,435,311 A | * | 7/1995 | Umemura et al. .............. | 601/3 |
| 5,558,092 A | * | 9/1996 | Unger et al. .................... | 600/439 |

* cited by examiner

Primary Examiner—Francis J. Jaworski
(74) Attorney, Agent, or Firm—Rothwell, Figg, Ernst & Manbeck

(57) ABSTRACT

Apparatus and method for early detection of cystic structures indicative of ovarian and breast cancers uses ultrasonic wave energy at a unique resonance frequency for inducing cavitation in cystic fluid characteristic of cystic structures in the ovaries associated with ovarian cancer, and in cystic structures in the breast associated with breast cancer. Induced cavitation bubbles in the cystic fluid implode, creating implosion waves which are detected by ultrasonic receiving transducers attached to the abdomen of the patient. Triangulation of the ultrasonic receiving transducers enables the received signals to be processed and analyzed to identify the location and structure of the cyst.

14 Claims, 3 Drawing Sheets

DETECTION OF CYSTIC STRUCTURES USING PULSED ULTRASONICALLY INDUCED RESONANT CAVITATION

CROSS REFERENCE TO RELATED APPLICATION

This application claims the benefit of the filing date of provisional application Ser. No. 60/149,901, filed Aug. 23, 1999.

GOVERNMENT RIGHTS STATEMENT

The invention described herein was made with government support under NASA Case No. 20623. The Federal Government has certain rights to this invention.

BACKGROUND OF THE INVENTION

1. Field of the Invention

This invention relates generally to medical diagnostic imaging, and more particularly to the use of ultrasonic wave generation for early detection of cystic structures in the body, such as in the breast or ovary, the presence of which may indicate the onset of breast cancer or ovarian cancer.

2. Description of Background Art

Breast cancer is the most common cancer and the second most common cause of cancer-related death in women, with 175,000 cases and 43,700 deaths projected in 1999 in the United States. Ovarian cancer is the fourth leading cause of cancer-related death among females in the United States, with over 25,000 new cases in 1998 and approximately half that number in deaths. When diagnosed at an early stage, there is a very high likelihood of cure for both diseases; however, because of the location and usually asymptomatic nature of even relatively advanced ovarian cancer, this type of cancer exhibits a high morbidity and mortality rate. Moreover, current methods of breast screening with physical examination and mammography still miss a significant number of breast cancers detectable by ultrasonography.

The presence of multiple cysts and fibronodular structures make precise characterization and accurate follow-up by physical examination and mammography problematic. The complex nature of the fibrocystic breast in premenopausal women is a particular challenge to the diagnostician, which should be especially amenable to characterization by the present invention. Conventional ultrasonography is useful for examination of a focal region but is neither efficient nor reproducible from operator to operator or from visit to visit by the same operator.

Over two decades ago, there was a major effort to assess the value of whole breast screening using automated ultrasonography methodologies. Unfortunately, there were both high false-positive and false-negative rates. Nevertheless, later studies demonstrated that ultrasonography can detect, at least in radiologically dense breasts, cancers not recognized by mammography and physical examination. Recently, one study found by ultrasonography only three cancers per thousand when screening 6113 women with dense breasts and no symptoms and 687 women with palpable or mammographically detected masses. In commenting on these studies, Kopans ("Breast Cancer Screening with Ultrasonography," Lancet 354 (9196):2096–7 (1999)) pointed out that although the independent rate of breast cancer detection by ultrasonography alone is not clear, the "possibility of ultrasonography for breast screening should not be ignored". The author further noted that handheld devices are operator dependent and expensive, requiring significant time by a radiologist, and concluded that automated ultrasonography devices are needed, if only to evaluate the usefulness of ultrasonography in improving breast cancer detection.

The present invention provides such a device, with novel ultrasonography features making the method rapid, accurate, reproducible and capable of automation. The device can be constructed so as to be able to compare standard ultrasonography images with selective induction of ultrasonic cavitation (SINUC) generated images and distinguish cystic from non-cystic structures.

There has yet to be clinically identified any pre-malignant condition which would presage the onset of ovarian cancer. Because most ovarian cancers are cystic in nature, the recognition of an irregular, septate, fluid-filled lesion in the ovary has been the focus of detection by the medical community. Various imaging technologies, including positron emission tomography (PET), radioimmunoscintography, magnetic resonance imaging (MRI), compute tomography (CT) scanning, and ultrasonography, all are capable of detecting cystic structures in the ovary.

The recent addition of color flow Doppler imaging in combination with transvaginal sonography appears to have added another level of sensitivity to the detection of ovarian abnormalities. Cohen and Jennings (Am J Obstet. Gyncol; 170:1088–1094) report that endovaginal probes at frequencies of 6.5 to 7.5 MHZ provide much finer discrimination of the ovary and uterus than is achievable with transabdominal ultrasonography. However, the use of various antigen markers, in particular Ca 125, in combination with transabdominal and transvaginal sonography, or (in one study) magnetic resonance imaging, has failed to achieve the levels of sensitivity and specificity necessary for a highly reliable screening technique.

There thus exists a need for a more sensitive, specific, and affordable technique for early detection of ovarian and breast cancers.

SUMMARY OF THE INVENTION

The present invention provides a solution to the existing need in the art by providing a noninvasive technique for the early detection of cystic structures using ultrasonic waves, potentially at the levels of microns. The present invention is based on the fact that most ovarian cancers and many breast cancers are cystic in nature, consisting of fluid-filled lesions, and on the observation by the present inventors that for any given fluid (characterized in terms of density, ultrasonic wave velocity, and viscosity), there exists a characteristic resonance frequency or frequency range and a threshold ultrasound power level at which cavitation bubbles are formed.

These cavitation bubbles are produced during the rarefaction phase of the ultrasonic wave, and implode to release shock waves at the pressure phase. The diameter of the cavitation bubbles depends upon the wavelength of the ultrasonic emission, and in the range of approximately 500 kHz it is on the order of several microns.

The induction of cavitation and the detection of the resulting implosion waves can be carried out transabdominally and noninvasively through the skin. The location of the cavitation source producing the implosion wave can be identified and used to create a three-dimensional image of the cystic fluid structure. The diagnostic procedure according to the invention is rapid, with minimum inconvenience to the patient, thus providing an affordable screening technique.

In particular, the present invention provides a method for identifying the presence of cystic structures in any tissue. A first specific application of the invention is as a method for recognizing the presence of cystic structures including ovarian cancers in the ovary. The method includes the steps of applying ultrasonic wave energy to a patient at a frequency causing induction of cavitation in cystic fluid characteristic of cancerous and other cystic structures in the tissues of humans, such as ovarian tissue, detecting implosion waves caused by the implosion of cavitation bubbles formed by the induction of cavitation, measuring the detected implosion waves, and determining the location of the cavitation source in the body of the patient. A second specific application of the invention is using SINUC to map cystic structures in the radiologically dense breast.

According to another aspect of the invention, apparatus for performing the method of detection of cystic structures is provided.

BRIEF DESCRIPTION OF THE DRAWINGS

The present invention can be more fully understood from the detailed description given below in conjunction with the accompanying drawings. These are provided by way of illustration only and are not intended as limiting the present invention, and wherein.

DETAILED DESCRIPTION OF THE PREFERRED EMBODIMENTS

Figure 1A:
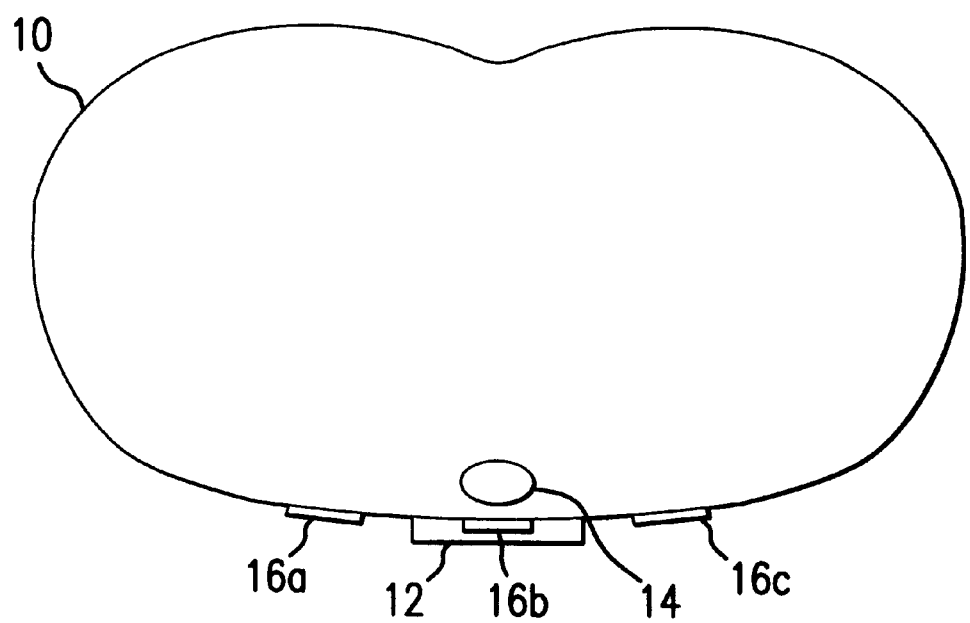
FIG. 1A is a cross sectional view of a patient's abdomen illustrating the placement of an ultrasonic transmitter and transducers according to one preferred embodiment of the invention.
Figure 1B:
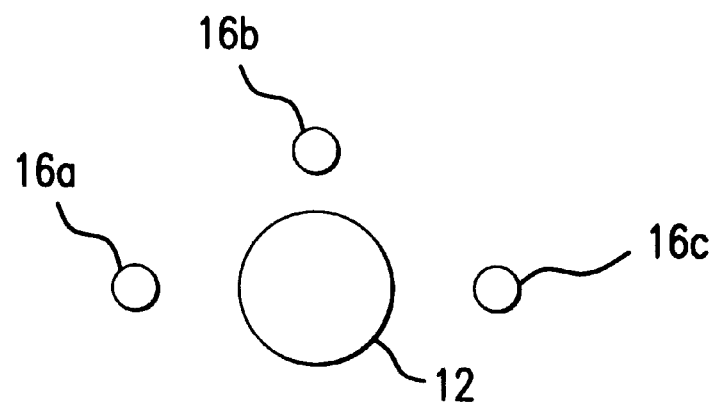
FIG. 1B is an elevational view of the placement of the ultrasonic transmitter and transducers of FIG. 1A.

Referring to FIGS. 1A–1B, according to one preferred embodiment, the invention provides a screening technique for early detection of ovarian cancers which utilizes an ultrasonic transmitter 12, and a plurality of receivers 16a, 16b, and 16c. In a preferred configuration, the receivers 16a–16c are arranged in a triangulation array in order to obtain three-dimensional location information of possible malignant structures in the ovary. As shown in FIG. 1A, the transmitter and receivers are placed on the abdomen of a patient 10, at a location opposite from ovary 14.

The screening technique relies upon the induced formation at characteristic resonant frequencies of cavitation bubbles in the fluid contained in the cystic structures associated with ovarian cancer. The induced cavitation forms implosion waves having a spectral content that is relatively easy to measure and to use to identify the location of the cavitation source.

Figure 5:
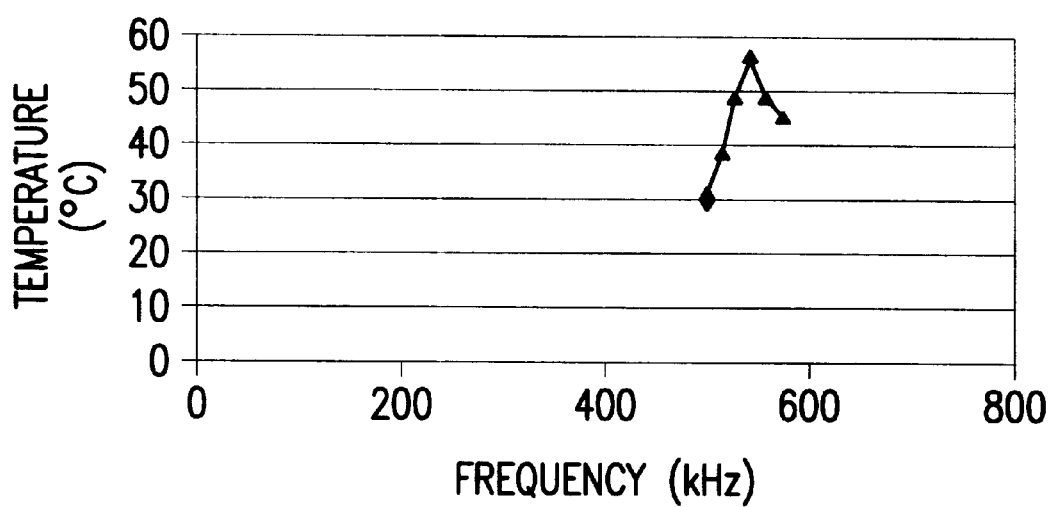
FIG. 5 is a graph showing the relationship between thermal induction caused by cavitation induced by ultrasonic wave and the frequency of the ultrasonic wave.

Experiments by the present inventors have shown that in water, a resonant response wave can be obtained at a frequency of 529 kHz. As shown in FIG. 5, the use of continuous ultrasonic waves at high energy cause extensive excitation of cavitation and thus increase the temperature to a maximum value at the resonance frequency. The location of the peak of temperature rise as shown in FIG. 5 coincides with a resonant induction of cavitation. Simultaneous measurement of the wave resulting from implosion of the cavitation bubbles, using a hydrophone transducer, showed a significant increase in amplitude at the same frequency.

The problem of wave propagation through tissues can be treated as a behavior in viscous fluid, which is described by the governing equation:

$$\rho_L \left[ \frac{\partial v}{\partial t} + (v \cdot \nabla)v \right] = -\nabla p + \left(\frac{4}{3}\eta + \eta_B\right)\nabla(\nabla \cdot v) + \eta \nabla \times \nabla \times v$$

Where: $\rho_L$ is fluid density; $\eta$ is shear viscosity; $\eta_B$ is bulk viscosity; p is pressure; and v is particle velocity.

To determine the pressure field of the ultrasonic wave, this equation needs to be solved using appropriate boundary conditions. Cavitations are formed when the pressure, p, drops below the critical vapor pressure of the fluid, p0. As the ultrasonic wave phase changes, the cavitations are imploded and their collapse characteristics can be analyzed using a modified Rayleigh-Plesset equation:

$$\left(1 - \frac{1}{c}\frac{dR}{dt}\right) R \frac{d^2 R}{dt^2} + \frac{3}{2}\left(1 - \frac{1}{3c}\frac{dR}{dt}\right)\left(\frac{dR}{dt}\right)^2 = \left(1 + \frac{1}{c}\frac{dR}{dt}\right)\frac{1}{\rho_L}\left[p_b - p_\infty - p_c\left(t + \frac{R}{c}\right)\right] + \frac{R}{\rho_L c}\frac{dp_b}{dt}$$

Where R is the radius of cavitation; c is sound velocity of the fluid; Pc, is pressure in the liquid at the location of the cavitation center in the absence of the cavitation; P∞ is the far field pressure; and Pb is internal pressure of the cavitation.

The viscosity of the liquid plays an important role in the formation of cavitation. The effect of viscosity is to cause damping and loss of mechanical energy during the growth and collapse process. Consequently, it is expected that an increase in viscosity will lead to a decrease in maximum cavity size and rate of growth and collapse. For liquids with different viscosity, the induced impulse level varies although each is activated by the same acoustic source. Moreover, different wave pressure is needed to form a vapor cavity in different liquids.

Modeling the cavitation phenomenon requires dealing with significant nonlinearity and heterogeneity. Nonlinearities arise from changes in temperature, pressure, stress, strain, strain rate, and other properties associated with the input ultrasonic wave. These changes dynamically affect the mechanical and thermal properties of the propagation medium, altering wave speed and attenuation. Solving partial differential equations with explicit non-linearity is complicated and time consuming. To avoid these difficulties, linear numerical methods are used. To obtain an analytical solution to the cavitation problem, incremental linearization can be used. For this type of time-dependent problem, "incrementally linear" means advancing the solution in time by discrete increments and modifying the material properties at the end of each increment. Time increments must be small enough that the solution is linear over each increment. Using this approach the response of cavitation can be determined and the effect of various related parameters can be incorporated. A computer simulation can be developed to examine the effect of changing liquid properties and input wave parameters on the induction of cavitation and emission of impulses. The frequency of the input wave can be optimized to produce small cavitation for high sensitivity of detection while accounting for the increased attenuation.

The transabdominal sonography using the transmitter as shown in FIGS. 1A–1B thus can selectively induce cavitation in the cystic fluids of the ovary, which in turn produces singularly detectable and identifiable implosion waves. Ultrasound energy is produced at energy levels and durations that does not result in tissue damage. The signals received by the transducers or receivers 16a–16c are used to create a three-dimensional image of ovarian cystic structures. The location of the cyst can be determined using well-established acoustic emission non-destructive testing method technology.

Figure 2:
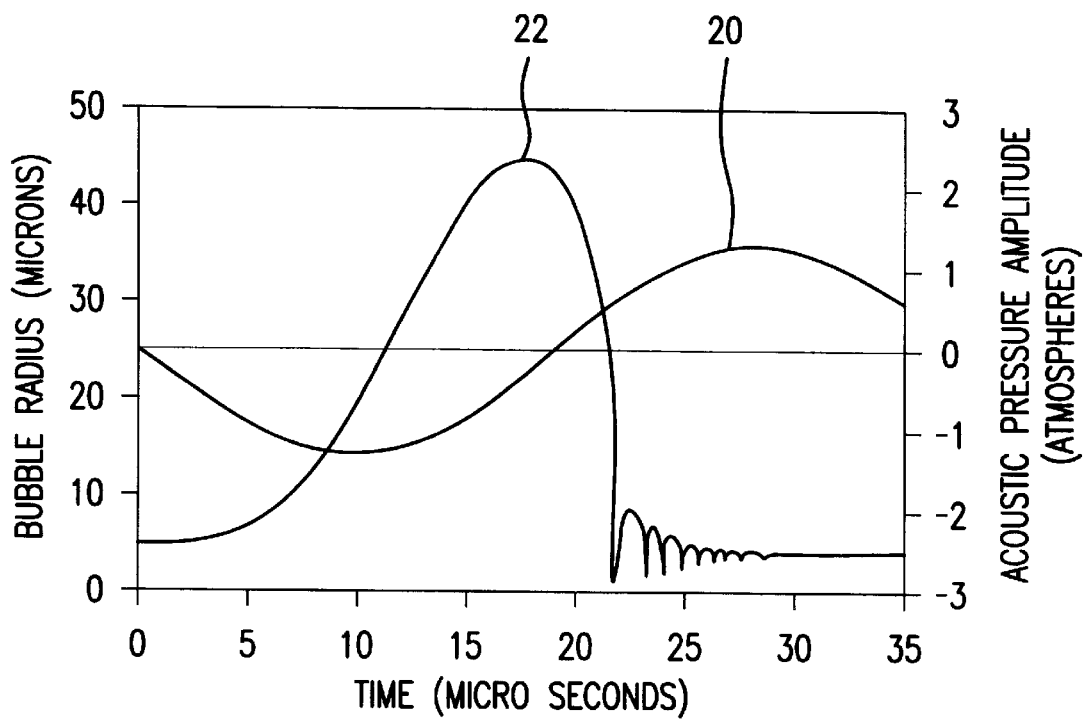
FIG. 2 is a graph illustrating the characteristics of induced cavitation bubbles with ultrasonic waves according to the invention.
Figure 3:
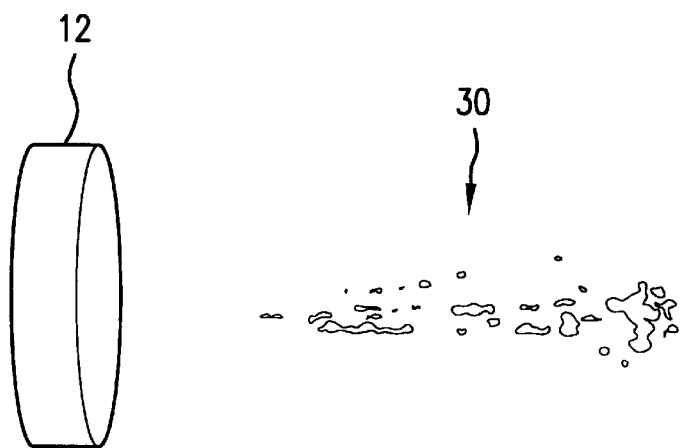
FIG. 3 is a representative illustration of an image formed by implosion waves produced from induced cavitation bubbles according to the invention.

FIG. 2 shows the relationship between the wavelength, phase and cavitation diameter, at a frequency of approximately 25 kHz. As shown, this results in the inducement of a cavitation bubble of approximately 45 microns in radius. Using a frequency on the order of several hundreds of kilohertz would lead to the induction of cavitation bubbles in the range of several microns. The particular resonance frequency for inducing cavitation in cystic fluid conditions representing human ovarian cysts can be identified by subjecting female patients to ultrasonic waves at various frequencies to identify the resonant frequency that uniquely identifies the ovarian cystic fluid. As stated above, in water this condition occurs at 529 kHz. FIG. 3 is an illustration showing the general character of cavitation bubbles induced by a focused ultrasonic transducer 12 using a continuous wave.

Figure 4:
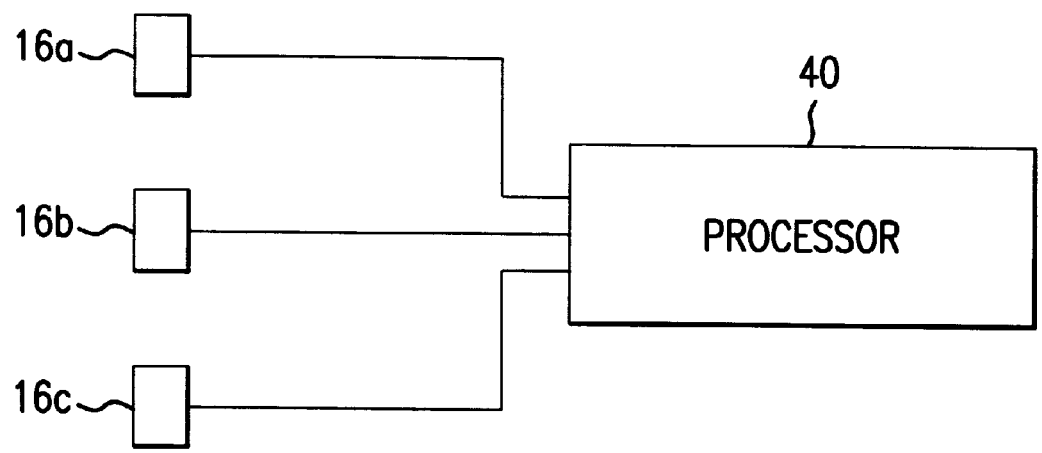
FIG. 4 is a block diagram of apparatus for analyzing detected cavitation waves to produce images, according to the invention.

In practice, as shown in FIG. 4, the signals from receiver transducers 16a–16c are inputted to a processor 40, such as a PC, workstation, or other computer, and are processed in conjunction with a triangulation algorithm to obtain a three dimensional image of the cystic structure(s) and its location. As shown in FIGS. 1A–1B, a number of receiving transducers are placed at preselected locations on the patient's abdomen, proximate the plane of the ovary 14. The received signals are analyzed and processed to determine the three-dimensional distribution of cavitation source sites. The control parameters of the ultrasonic waves (including pulse rate, duration, amplitude and center frequency) are determined in advance through experimentation, and are selected to ensure that no damage to tissue or to internal organs results from the application of ultrasonic energy. To ensure that the ultrasonic wave does not produce a significant temperature rise in the patient's tissues, short pulses on the order of milliseconds or shorter are used. The control parameters are selected to enable the ultrasonic waves to reach the cavitation excitation threshold level and to selectively induce cavitation in cystic fluid in a manner that maximizes screening sensitivity. Suitable in vivo experimentation can be carried out using artificial cysts of known density in order to identify the values of such control parameters. The identification of a unique resonance frequency for the induction of cavitation in ovarian cysts with minimum excitation in surrounding tissues and organs thus enables the early detection of ovarian cancers at sizes on the order of several microns, thereby significantly increasing the chances for cure by medical intervention at an early stage.

The novel method of the present invention offers a highly sensitive, rapid, non-invasive screening method for patients at high risk for ovarian cancer, and for tracking changes in the size and structures of known abnormalities. A follow-up transvaginal sonography test can be made for detailed evaluation when the ultrasonic screening method of the invention indicates the presence of a potential malignancy.

A similar transmitter-receiver configuration can be implemented for whole breast scanning.

The method of the present invention also can be used to identify the presence of cystic structures in any human tissue, in addition to ovarian tissue and breast tissue, and therefore may be used in other diagnostic procedures to identify such structures.

The invention having been thus described, it be apparent to those skilled in the art that the same may be varied in many ways without departing from the spirit and scope of the invention. Accordingly, any and all such modifications are intended to be covered by the following claims.

What is claimed is:

1. A method for identifying cystic structures in human tissue, comprising the steps of:

applying ultrasonic wave energy to a patient at a frequency causing induction of cavitation in cystic fluid characteristic of cystic structures in human tissue;

detecting implosion waves caused by the implosion of cavitation bubbles formed by said induction of cavitation;

measuring the detected implosion waves to detect the existence of a cystic structure; and determining the location of the cavitation source in the body of the patient from the measured implosion waves.

2. The method of claim 1, wherein the method is used to identify cystic structures in the ovary of a patient, and the step of applying comprises the step of attaching an ultrasonic wave generating transducer to the abdomen of the patient, in the plane of an ovary of the patient.

3. The method of claim 2, wherein the step of detecting comprises the step of attaching at least one ultrasonic receiving transducer to the abdomen of the patient in the plane of said ovary.

4. The method of claim 3, wherein the step of detecting further comprises the step of attaching a second and third ultrasonic receiving transducer to the abdomen of the patient, one of said second and third receiving transducers being located above the plane of said ovary and the other being located in the plane of said ovary together with said first receiving transducer.

5. The method of claim 1, wherein the frequency of said ultrasonic wave energy is on the order of hundreds of kilohertz.

6. The method of claim 1, wherein the method is used to identify cystic structures in the breast of a patient, and the step of applying comprises the step of attaching an ultrasonic wave generating transducer to the breast of the patient.

7. The method of claim 6, wherein the step of detecting comprises the step of attaching at least one ultrasonic receiving transducer to the breast of the patient.

8. Apparatus for identifying cystic i n tissue, comprising:

an ultrasonic wave generator that applies ultrasonic wave energy to a patient at a frequency causing induction of cavitation in cystic fluid characteristic of cystic structures in human tissue;

at least one ultrasonic wave receiver that detects implosion waves caused by the implosion of cavitation bubbles formed by said induction of cavitation;

a signal processor measuring the detected implosion waves to detect the existence of a cystic structure, and for determining the location of the cavitation source in the body of the patient from the measured implosion waves.

9. Apparatus according to claim 8, wherein said cystic structures are present in the human ovary, and are indicative of the presence of ovarian cancer, and wherein said ultrasonic wave generator comprises an ultrasonic wave generating transducer attachable to the abdomen of the patient, in the plane of an ovary of the patient.

10. Apparatus according to claim 9, wherein said at least one ultrasonic wave receiver comprises a receiving transducer attachable to the abdomen of the patient in the plane of said ovary.

11. Apparatus according to claim 10, further comprising second and third ultrasonic receiving transducers attachable to the abdomen of the patient, one of said second and third receiving transducers being located above the plane of said ovary and the other being located in the plane of said ovary together with said first receiving transducer.

12. Apparatus according to claim 8, wherein the frequency of said ultrasonic wave energy is on the order of hundreds of kilohertz.

13. Apparatus according to claim 8, wherein said cystic structures are present in the human breast, and are indicative of the presence of breast cancer, and wherein said ultrasonic wave generator comprises an ultrasonic wave generating transducer attachable to the breast of the patient.

14. Apparatus according to claim 13, wherein said at least one ultrasonic wave receiver comprises a receiving transducer attachable to the breast of the patient.

* * * * *

UNITED STATES PATENT AND TRADEMARK OFFICE
CERTIFICATE OF CORRECTION

PATENT NO. : 6,406,429 B1  Page 1 of 1
DATED : June 18, 2002
INVENTOR(S) : Bar-Cohen et al.

It is certified that error appears in the above-identified patent and that said Letters Patent is hereby corrected as shown below:

<u>Column 6,</u>
Line 53, "i n" should be read -- structures in human --

Signed and Sealed this

First Day of June, 2004

JON W. DUDAS
*Acting Director of the United States Patent and Trademark Office*